(12) United States Patent
Muller-Aufferman et al.

(10) Patent No.: US 11,760,964 B2
(45) Date of Patent: *Sep. 19, 2023

(54) PLANT FAT-BASED SCAFFOLDS FOR THE GROWTH OF CELL-BASED MEATS AND METHODS OF MAKING SUCH PRODUCTS

(71) Applicant: Upside Foods, Inc., Berkeley, CA (US)

(72) Inventors: Konrad Muller-Aufferman, Berkeley, CA (US); Michaela Walker, Berkeley, CA (US)

(73) Assignee: Upside Foods, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/572,297

(22) Filed: Jan. 10, 2022

(65) Prior Publication Data

US 2022/0403310 A1    Dec. 22, 2022

Related U.S. Application Data

(63) Continuation of application No. 17/304,235, filed on Jun. 16, 2021.

(51) Int. Cl.
| | |
|---|---|
| *C12M 3/00* | (2006.01) |
| *C12N 5/077* | (2010.01) |
| *C12M 1/12* | (2006.01) |
| *C12M 1/00* | (2006.01) |
| *A23L 13/00* | (2016.01) |
| *A23L 33/17* | (2016.01) |
| *A23L 33/15* | (2016.01) |
| *A23L 33/16* | (2016.01) |
| *A23L 33/12* | (2016.01) |

(52) U.S. Cl.
CPC ............ *C12M 21/08* (2013.01); *A23L 13/00* (2016.08); *A23L 33/12* (2016.08); *A23L 33/15* (2016.08); *A23L 33/16* (2016.08); *A23L 33/17* (2016.08); *C12M 25/14* (2013.01); *C12M 37/06* (2013.01); *C12M 47/02* (2013.01); *C12N 5/0658* (2013.01); *A23V 2002/00* (2013.01); *C12N 2533/90* (2013.01); *C12N 2539/00* (2013.01)

(58) Field of Classification Search
CPC ...... C12M 21/08; C12M 25/14; C12M 37/06; C12M 47/02; A23L 13/00; A23L 33/12; A23L 33/17; C12N 5/0658; C12N 2533/90; C12N 2539/00; A23V 2002/00
See application file for complete search history.

(56) References Cited

U.S. PATENT DOCUMENTS

| | | | |
|---|---|---|---|
| 9,752,122 B2 | 9/2017 | Marga et al. | |
| 9,974,886 B2* | 5/2018 | Wang | ................ A61L 27/3817 |
| 2010/0196432 A1 | 8/2010 | Feinberg et al. | |
| 2011/0270400 A1* | 11/2011 | Kita | ........................ A61L 27/52 |
| | | | 523/113 |
| 2013/0029008 A1* | 1/2013 | Forgacs | ................... A23L 13/03 |
| | | | 426/55 |
| 2015/0079238 A1* | 3/2015 | Marga | ...................... A23P 10/20 |
| | | | 426/577 |
| 2015/0157038 A1* | 6/2015 | Ergun | ..................... A23G 1/305 |
| | | | 426/573 |
| 2015/0202586 A1* | 7/2015 | Imoto | .................. A61K 9/0009 |
| | | | 516/103 |
| 2016/0145311 A1* | 5/2016 | Shoseyov | ............ A61K 31/717 |
| | | | 435/320.1 |
| 2017/0105438 A1* | 4/2017 | Ajami | ..................... A23L 33/17 |
| 2019/0343889 A1* | 11/2019 | Luukko | ............... A61L 24/0036 |
| 2020/0157506 A1 | 5/2020 | Bayer et al. | |
| 2021/0046220 A1* | 2/2021 | Alsberg | .............. A61L 27/3834 |
| 2021/0139843 A1* | 5/2021 | Nah | ........................ C12M 29/10 |
| 2022/0125072 A1* | 4/2022 | Ben-Shitrit | ............. A23P 20/20 |

FOREIGN PATENT DOCUMENTS

| | | | | |
|---|---|---|---|---|
| WO | WO-2017035332 A1 * | 3/2017 | ............... | A61F 2/30 |
| WO | WO 2018189738 A1 | 10/2018 | | |
| WO | WO 2018227016 A1 | 12/2018 | | |
| WO | WO-2020030628 A1 * | 2/2020 | ............. | A23D 9/013 |
| WO | WO-2020123876 A1 * | 6/2020 | ............. | A23L 13/00 |
| WO | WO-2020170196 A1 * | 8/2020 | ........... | A61K 31/722 |
| WO | WO 2020219755 A1 | 10/2020 | | |
| WO | WO 2020222239 A1 | 11/2020 | | |
| WO | WO 2020227835 A1 | 11/2020 | | |
| WO | WO-2020249734 A1 * | 12/2020 | ............. | A61K 35/74 |

OTHER PUBLICATIONS

Limbardo et al. "The effect of coconut oil and palm oil as substituted oils to cocoa butter on chocolate bar texture and melting point." AIP Conference Proceedings 1840, 060001 (2017) (Year: 2017).*
Wu et al. "Effects of storage culture media, temperature and duration on human adipose-derived stem cell viability for clinical use." Mol Med Rep .Mar. 2019; 19(3):2189-2201. (Year: 2019).*
Edelman et al. "Commentary: In vitro-cultured meat production"Tissue Eng .May-Jun. 2008;11(5-6):659-62. (Year: 2005).*
Chriki et al. "The Myth of Cultured Meat: A Review"Front Nutr. 2020; 7: 7. (Year: 2020).*
Fish et al. "Prospects and challenges for cell-cultured fat as a novel food ingredient."Trends Food Sci Technol . Apr. 2020;98:53-67. (Year: 2020).*

(Continued)

*Primary Examiner* — Titilayo Moloye
(74) *Attorney, Agent, or Firm* — Keller Preece PLLC

(57) ABSTRACT

A plant fat-based scaffold for growing cell-based meat products for consumption. The scaffold comprises primarily plant fats or waxes in addition to cell binding proteins and optional additional components that assist in the growth of cultivated animal cells. The scaffold can exist in both a liquified state during sterilization and a solid state during the formation of the scaffold, the seeding of the cultivated cells, and the cellular growth phase. The scaffold is capable of remaining in the final product for consumption or is partially or completely melted out of the final product and recycled into raw material for forming new scaffolds.

20 Claims, 1 Drawing Sheet

(56) References Cited

OTHER PUBLICATIONS

Guan et al. "Bioprocessing technology of muscle stem cells: implications for cultured meat."Trends Biotechnol . Jun. 2022;40(6):721-734. (Year: 2022).*

Jaganathan et al., Manufacturing and Characterization of Novel Electrospun Composite Comprising Polyurethane and Mustard Oil Scaffold with Enhanced Blood Compatibility, Polymers, May 4, 2017, vol. 9, MDPI, Basel, Switzerland (11 pages).

De Carvalho et al., Biocompatibility of Mesenchymal Stem Cells in Wharton's Jelly of Caprine In Porous Matrix of Buriti Oil (*Maurita flexuosa*), Politica, Planejamento, e Gestao em Saude, Jun. 5, 2020, Atena Editora, Brazil (13 pages).

Lukyanova et al., Preparation and Evaluation of Microporous Organogel Scaffolds for Cell Viability and Proliferation, Colloids and Surfaces B: Biointerfaces, Apr. 8, 2010, vol. 79, Elsevier, Amsterdam, Netherlands, pp. 105-112.

International Search Report & Written Opinion as received in PCT/US2021/037688 dated May 20, 2022.

\* cited by examiner

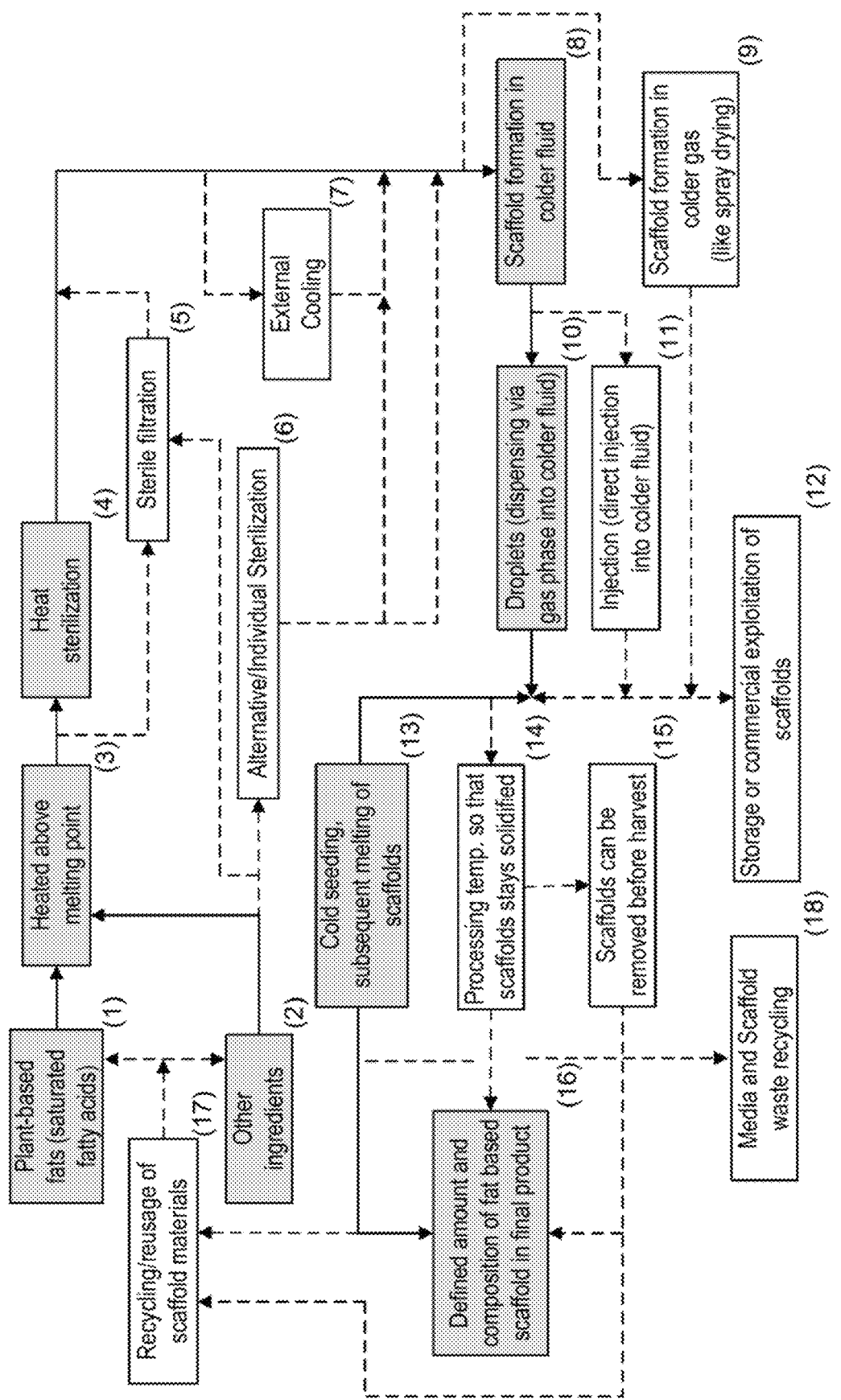

PLANT FAT-BASED SCAFFOLDS FOR THE GROWTH OF CELL-BASED MEATS AND METHODS OF MAKING SUCH PRODUCTS

CROSS-REFERENCE TO RELATED APPLICATION

This is a continuation of U.S. application Ser. No. 17/304,235, filed Jun. 16, 2021, the entire contents of which are incorporated herein by reference.

TECHNICAL FIELD

This invention is in the field of cell-based products for consumption, in particular, a product for consumption prepared from a combination of cultivated adherent and suspension cells derived from a non-human animal. The present disclosure relates to novel consumable products and methods of preparing such consumable products.

BACKGROUND

As the world's population continues to grow, the need for products for human consumption is greater than ever. That being said, given the expanding population, the market of conventional products is struggling to meet the demand. In vitro produced cell-based products for consumption have emerged as an attractive option to supplement the demand for conventional products. Moreover, in vitro produced products help alleviate several drawbacks linked to conventional products. For instance, conventional meat production involves controversial practices associated with animal husbandry and slaughter. Other drawbacks associated with conventional meat production include low conversion of caloric input to edible nutrients, microbial contamination of the product, emergence and propagation of veterinary and zoonotic diseases, relative natural resource requirements, and resultant industrial pollutants, such as greenhouse gas emissions and nitrogen waste streams.

Lab-grown or cultured meat belongs to the emerging field of cellular agriculture and represents a promising technology for delivering products that have so far been produced through livestock. This technological innovation aims to offer a possibility of reducing the negative effects of conventional meat production techniques on humans, livestock, and the environment. The production of cultured meat requires suitable cells and appropriate growth media. Lab-grown meat could also be an excellent functional food to cover specific dietary needs for people with various ailments. This is due to the capability of the technology to modify the profile of essential amino acids and fats and to be enriched in vitamins, minerals, and bioactive compounds. However, there are various technical questions associated with growing and processing cultured meat.

For the growth of typical, texture relevant muscle fibers with multiple nuclei, it is important that cells bond, to enable signaling, protein excretion and fusion. Scaffolds can be introduced to the cellular growth environment to further enable adherence and cell communication. For example, grown cell sheets of cultured meat require a support structure, such as a scaffold, which is capable of being sterilized to prevent contamination of the cultured meat, capable of allowing the cell sheets to access critical nutrients during growth, and capable of being removed without damaging the structure of the meat and/or the substrate.

However, the majority of known scaffolds, which are commonly used for medical purposes, are designed based solely on functionality and use non-edible ingredients. Such scaffolds cannot be eaten and must be completely removed from the cell-based meat products prior to human consumption, which can be both time-consuming and resource-expensive. Thus, it is an object of the invention to provide consumable scaffolds prepared from edible, plant-based products that are capable of providing the necessary structure and growth support for cell-based meat products and methods of producing such scaffolds.

SUMMARY

This invention generally relates to scaffolds used for the growth of cell-based meat products for consumption. In some embodiments, the scaffolds are created primarily from plant-based fats which are safe for consumption and are capable of forming solid structures that provide the necessary support for the growth of the cell-based meats. An exemplary method of creating the scaffolds includes, but is not limited to, use of a self-contained bioreactor, as described below. Other exemplary methods of creating the scaffold include using a 3D printer, or on a benchtop, in a sterilized environment. In some embodiments, the scaffold can take on a variety of shapes depending on the method of delivery of the scaffold into the self-contained bioreactor. For example, the scaffold can be spray dried into the bioreactor in the form of droplets or injected into the bioreactor directly via a nozzle to form spaghetti like strands. A combination of these different scaffold shapes can also be utilized simultaneously.

In all embodiments, natural plant-based fats and waxes are hereby used as scaffold ingredients. The scaffold may comprise a combination of different types of plant-based fats and waxes, each with varying melting point properties. As these materials are hydrophobic and cells do not attach onto them in their pure form, other functional ingredients like cell-binding proteins, carbohydrates, fibers and/or minerals are added to the plant fat-based scaffold to better assist the attachment of the cells to the scaffold, improve the growth rate of the cells on the scaffold, or to maintain the stability of the scaffold structure, preferably under hot and sterile conditions. These ingredients can be added to the scaffold either while the scaffold is in a liquid state or while it is in a solid state.

All ingredients of the scaffold can be sterilized using known methods of sterilization prior to inclusion in a scaffold. Exemplary methods of sterilization include, but are not limited to, using heat, filtration, or a combination of both. In one embodiment, the plant fat-based ingredients are melted into a liquid state and sterilized by heat before being filtered through a sterile filtration system. Heat sterilization may involve heating the plant fat-based ingredients to a sterilization temperature between 35 degrees Celsius up to 100 degrees Celsius, and holding the raised temperature for a specific time to ensure sterilization. Generally speaking, the higher the sterilization temperature, the shorter the amount of time required for the ingredients to be held at sterilization temperature. Using heat sterilization combined with sterile filtration on the liquified plant fat-based ingredients is a more efficient process as liquids are generally easier to sterilize than solid ingredients. Furthermore, heating the liquified plant fat-based ingredients affects the viscosity of the liquified components, making them easier to filter through the sterile filtration system. The other functional ingredients may be added to the plant fat suspension and sterilized alongside the plant fat-based ingredients or separately sterilized individually.

In some embodiments, after the ingredients are sterilized, the suspension containing the ingredients is cooled down to an incorporation temperature before scaffold formation. The incorporation temperature will vary depending on the types of cells that are desired to be grown. The incorporation temperature is the temperature range where the scaffold solidifies, cell adherence is optimal, or some combination of either event. The incorporation temperature will vary depending on the types of cells that are desired to be grown. Generally, the incorporation temperature is between 10 degrees to 40 degrees Celsius. When using cells with higher optimal growth temperature, the incorporation temperature may also rise correspondingly. In some embodiments, the heated suspension is cooled via the use of cold gases to solidify the suspension into a scaffold. In other embodiments, the suspension is dispersed into a cold, sterile fluid which causes the suspension to solidify into a scaffold. The suspension can either be injected directly into the cold fluid or it can be sprayed into the fluid to create a high number of droplets with a large surface area for cell adherence. In a preferred embodiment, the suspension is cooled and formed into a scaffold at temperatures in which the seeded cells can bind to the scaffold and fuse to form the desired tissue.

The cell seeding may be performed at the incorporation temperature. The incorporation temperature may be lower than the optimal cellular growth temperature, and cell seeding below this temperature may ensure that the entirety of the scaffold remains solid. Alternatively, cell seeding may be performed at a higher temperature than the incorporation temperature to ensure that the scaffold remains partially or completely liquid. Optimal cellular growth temperature can fluctuate depending on the type of cells desired to be grown. For example, mammalian cells are typically grown in an environment around 35 to 37 degrees Celsius while fish cells prefer a colder environment of around 15 to 20 degrees Celsius. After the seeding step is complete, the cells are immersed into a nutrient rich environment. The temperature is then gradually raised to reach the optimal growth temperature for the seeded cells. In embodiments where the entire structure of the scaffold is not required to provide stability to the cells, the temperature is raised to the point where a portion of the scaffold melts, which releases additional nutrients that benefit cellular growth and further exposes the cells to the nutrient rich environment. In alternative embodiments, the scaffold is constructed from one or more fats, one or more waxes, or some combination thereof that have a relatively high melting point, whereby raising the temperature to the optimal growth temperature does not result in the scaffold melting. In one example, the scaffold is constructed from two or more different types of fats or waxes, each having different melting temperatures, to expand the temperature range between partial scaffold melting and complete scaffold melting. In some instances, the cell seeding stage may be performed at a higher temperature than the optimal growth temperature of the seeded cells but below the upper end of the temperature endurance range of the cells to ensure that the scaffold is at an at least partially melted state, before the addition of the cellular binding proteins. he temperature may then be lowered to the optimal growth temperature of the seeded cells. The temperature endurance range of mammalian cells for extended periods of time is generally between 20-55 degrees Celsius, while the temperature endurance range of cold-blooded cells (including fish) for extended periods of time is generally between 10 to 40 degrees Celsius. In some instances, mammalian cells and cold-blooded cells may be kept at 4 degrees Celsius for short time periods, e.g., overnight, with no adverse impact on growth or survival rate once returned to optimal temperatures.

In some embodiments, after reaching the desired biomass and degree of tissue formation/cell fusions, the entire scaffold or a portion thereof can be left in the final product, as it is edible. In other embodiments, the plant-fat based scaffolds have a melting point lower than the upper end of the temperature endurance range, whereby the scaffold may be partially or completely melted out before the cell tissue is harvested without damaging the cell tissue. The melted scaffold can either be recycled via conventionally known methods (for example in wastewater treatment plants) or the melted scaffold may be reused as new scaffold material for subsequent batches.

BRIEF DESCRIPTION OF THE DRAWINGS

FIG. 1 depicts an exemplary flowchart demonstrating the creation of the scaffold.

DETAILED DESCRIPTION

Provided herein are methods and products related to the preparation of plant fat-based scaffolds for the growth of cell-based meats.

Before describing particular embodiments in detail, it is to be understood that the disclosure is not limited to the particular embodiments described herein, which can vary. It is also to be understood that the terminology used herein is for the purpose of describing particular illustrative embodiments only, and is not intended to be limiting unless otherwise defined. The terms used in this specification generally have their ordinary meaning in the art, within the context of this disclosure and in the specific context in which each term is used. Certain terms are discussed below or elsewhere in the specification, to provide additional guidance to the practitioner in describing the compositions and methods of the invention and how to make and use them. The scope and meaning of any term will be apparent from the specific context in which the term is used. As such, the definitions set forth herein are intended to provide illustrative guidance in ascertaining particular embodiments of the invention, without limitation to particular compositions or biological systems.

As used in the present disclosure and the appended claims, the singular forms "a," "an" and "the" include plural references unless the content clearly dictates otherwise.

Unless specific definitions are provided, the nomenclature utilized in connection with, and the laboratory procedures and techniques of, molecular biology, cell biology, analytical chemistry, and synthetic organic chemistry described herein are those well-known and commonly used in the art. Standard techniques may be used for recombinant technology, molecular biological, microbiological, chemical syntheses, and chemical analyses.

Generation of Cell-Based Products for Consumption

The cell-based products for consumption of the disclosure are products produced by the in vitro culturing of naturally occurring, transgenic, or modified animal cells in culture.

The cells used in the methods of the present disclosure can be primary cells, or cell lines. The methods provided herein are applicable to any metazoan cell in culture. Generally, the cells are from any metazoan species whose tissues are suitable for dietary consumption, and demonstrate the capacity for skeletal muscle tissue specification.

In some embodiments, the cells are derived from any non-human animal species intended for human or non-human dietary consumption (e.g., cells of avian, ovine, caprine, porcine, bovine, or piscine origin) (e.g., cells of livestock, poultry, avian, game, or aquatic species).

In some embodiments, the cells are from livestock such as domestic cattle, pigs, sheep, goats, camels, water buffalo, rabbits and the like. In some embodiments, the cells are from poultry such as domestic chicken, turkeys, ducks, geese, pigeons and the like. In some embodiments, the cells are from game species such as wild deer, gallinaceous fowl, waterfowl, hare and the like. In some embodiments, the cells are from aquatic species or semi-aquatic species harvested commercially from wild fisheries or aquaculture operations, or for sport, including certain fish, crustaceans, mollusks, cephalopods, cetaceans, crocodilians, turtles, frogs and the like.

In some embodiments, the cells are from exotic, conserved or extinct animal species. In some embodiments, the cells are from *Gallus gallus, Gallus domesticus, Bos taurus, Sous scrofa, Meleagris gallopavo, Anas platyrynchos, Salmo salar, Thunnus thynnus, Ovis aries, Coturnix, Capra aegagrus hircus*, or *Homarus americanus*.

In some embodiments, the cells are primary stem cells, self-renewing stem cells, embryonic stem cells, pluripotent stem cells, induced pluripotent stem cells, or trans-differentiated pluripotent stem cells.

In some embodiments, the cells are modifiable by a genetic switch to induce rapid and efficient conversion of the cells to skeletal muscle for cultured production.

In some embodiments, the cells are myogenic cells, destined to become muscle, or muscle-like cells. In some embodiments, the myogenic cells are natively myogenic, e.g., myoblasts. Natively myogenic cells include, but are not limited to, myoblasts, myocytes, satellite cells, side population cells, muscle derived stem cells, mesenchymal stem cells, myogenic pericytes, or mesoangioblasts.

In some embodiments, cells are of the skeletal muscle lineage. Cells of the skeletal muscle lineage include myoblasts, myocytes, and skeletal muscle progenitor cells, also called myogenic progenitors that include satellite cells, side population cells, muscle derived stem cells, mesenchymal stem cells, myogenic pericytes, and mesoangioblasts.

In some embodiments, the cells are non-myogenic, and such non-myogenic cells can be programmed to be myogenic, for example, the cells may comprise fibroblasts modified to express one or more myogenic transcription factors. In exemplary embodiments, the myogenic transcription factors include MYOD1, MYOG, MYF5, MYF6, PAX3, PAX7, paralogs, orthologs, and genetic variants thereof. In some embodiments, the cells are modified to express one or more myogenic transcription factors as described in a PCT publication, WO/2015/066377, incorporated by reference herein in its entirety.

In some embodiments, the cells comprise a mixture of cell populations described herein, e.g., a mixture of fibrogenic cells and myogenic cells in co-culture, e.g., a mixture of fibroblasts and myoblasts in co-culture. In some embodiments, the cells used for the in vitro production of cell-based products for consumption are a mixture of fibroblasts and myoblasts in a suspension co-culture. In some embodiments the cells used for the in vitro production of cell-based products for consumption are a mixture of fibroblasts and myoblasts in an adherent co-culture. In some embodiments, the co-culture can further comprise adipocytes.

In some embodiments, the cells are in either a suspension culture or adherent co-culture, and comprise a mixture of fibroblasts and myoblasts, wherein the ratio of the fibroblasts to myoblasts (designated as F and M) ranges from about 5F:95M to about 95F:5M. In exemplary embodiments, the ratio of the fibroblasts to myoblasts is about 5F:95M, 10F:90M, 15F:85M, 20F:80M, 25F:75M, 30F:70M, 35F:65M, 40F:60M, 45F:55M, 50F:50M, 55F:45M, 60F:40M, 65F:35M, 70F:30M, 75F:25M, 80F:20M, 85F:15M, 90F:10M, or even about 95F:5M.

In some embodiments, the cells are genetically modified to inhibit a pathway, e.g., the HIPPO signaling pathway. Exemplary methods to inhibit the HIPPO signaling pathway as described in a PCT Application No. PCT/US2018/031276, incorporated by reference herein in its entirety.

In some embodiments, the cells are modified to express telomerase reverse transcriptase (TERT) and/or inhibit cyclin-dependent kinase inhibitors (CKI). In some embodiments, the cells are modified to express TERT and/or inhibit cyclin-dependent kinase inhibitors as described in a PCT publication, WO 2017/124100, incorporated by reference herein in its entirety.

In some embodiments, the cells are modified to express glutamine synthetase (GS), insulin-like growth factor (IGF), and/or albumin. Exemplary methods of modifying cells to express GS, IGF, and/or albumin are described in a PCT Application No. PCT/US2018/042187 which is incorporated by reference herein in its entirety.

In some embodiments, the cells may comprise any combination of the modifications and cells described herein.

Cultivation Infrastructure

As referred to herein, a cultivation infrastructure refers to the environment in which the cells are cultured or cultivated to provide a two-dimensional or three-dimensional product for consumption.

A cultivation infrastructure may be a roller bottle, a tube, a cylinder, a flask, a petri-dish, a multi-well plate, a dish, a vat, an incubator, a bioreactor, an industrial fermenter and the like.

While the cultivation infrastructure itself may have a three-dimensional structure or shape, the cells cultured in the cultivation infrastructure may form a monolayer of cells. Compositions and methods of the present disclosure can promote a three-dimensional growth of metazoan cells in the cultivation infrastructure to provide a scaffold-less self-assembly of a three-dimensional cellular biomass.

A three-dimensional cultivation infrastructure may be sculpted into different sizes, shapes, and forms, as desired, to provide the shape and form for the muscle cells to grow and resemble different types of muscle tissues such as steak, tenderloin, shank, chicken breast, drumstick, lamb chops, fish fillet, lobster tail, etc. The three-dimensional cultivation infrastructure may be made from natural or synthetic biomaterials that are non-toxic so that they may not be harmful if ingested. Natural biomaterials may include, for example, collagen, fibronectin, laminin, or other extracellular matrices. Synthetic biomaterials may include, for example, hydroxyapatite, alginate, polyglycolic acid, polylactic acid, or their copolymers. The three-dimensional cultivation infrastructure may be formed as a solid or semisolid support.

A cultivation infrastructure can be of any scale, and support any volume of cellular biomass and culturing reagents. In some embodiments, the cultivation infrastructure ranges from about 10 µL to about 100,000 L. In exemplary embodiments, the cultivation infrastructure is about 10 µL, about 100 µL, about 1 mL, about 10 mL, about 100 mL, about 1 L, about 10 L, about 100 L, about 1000 L, about 10,000 L, or even about 100,000 L.

In some embodiments, the cultivation infrastructure comprises a scaffold. A cultivation infrastructure may comprise a permeable scaffold (e.g., permeable to physiological solutions) or an impermeable scaffold (e.g., impermeable to physiological solutions). The scaffold can be flat, concave, or convex. The scaffold may be textured so as to promote cell growth and cell sheet attachment. Benefits of using such a scaffold include reducing the cost of production by removing the requirement of using additional cell cultures to form an autologous scaffold, being able to control the shape and size of the scaffold, being able to form shapes and structures not physically possible only using components producible by a cell (e.g. ECM), being able to quickly form the necessary structures (as cellular production of such structures may be very slow), and being able to incorporate additional components, such as nutrients beneficial to cellular growth, into the scaffold itself to promote the cellular growth phase.

In some embodiments, the culturing of cells in the cultivation infrastructure can induce the production of extracellular matrix (ECM) that may act as an autologous scaffold to direct three-dimensional cellular growth, e.g., to direct attachment, proliferation and hypertrophy of cells on a plane perpendicular to the substrate.

In some embodiments, the cultivation infrastructure may not comprise an exogenously added scaffold to promote self-assembly of a three-dimensional cellular biomass. In some embodiments, the cultivation infrastructure may not comprise exogenous scaffolds such as a plant fat-based scaffold as described herein, a hydrogel, or soft agar.

Culturing Conditions

The culturing conditions for the generation of cell-based products for consumption are generally aseptic, and sterile.

Cells can be grown in an adherent culture format to form a cell sheet or can be grown in a suspension culture format to form a cell pellet. Table 1 provides exemplary culture methods for the various products that can be produced in vitro.

culturing the fibroblasts and/or myoblasts in media under conditions under which the fibroblasts and/or myoblasts grow in either suspension culture or adherent culture, wherein the media is substantially free of serum and other components derived from an animal.

In some embodiments, the cells are grown in a suspension culture, e.g., in a shake flask, and the product of the culture is centrifuged, yielding a cell pellet. In other embodiments, the cells are grown in adherent culture, and the product of the culture is a cell sheet.

Formulation

The consumable cell-based products of the disclosure may be processed into any variety of products including, but not limited to, cell-based meat products, supplements, and vitamins. Exemplary products of the disclosure include cell-based meat products, such as, for example, avian meat products, chicken meat products, duck meat products, and bovine meat products. Other exemplary products may include cell-based meat products cultivated using cells from exotic, conserved or extinct animal species such as, but not limited to, *Gallus gallus, Gallus domesticus, Bos taurus, Sous scrofa, Meleagris gallopavo, Anas platyrynchos, Salmo salar, Thunnus thynnus, Ovis aries, Coturnix, Capra aegagrus hircus*, or *Homarus americanus*.

Characteristics of Cell-Based Products for Consumption

Provided herein are in vitro produced cell-based products for consumption comprising a number of unique features that allow them to be distinguished from conventional products (which can involve the slaughter or demise of live animals). The in vitro methods can also be tailored to achieve desired traits such as health and sensory benefits.

Hormones

As compared to conventional products, the in vitro produced cell-based products of the disclosure comprise a significantly lower amount of steroid hormones. For example, using the in vitro culturing methods described, there need not be any exogenous hormones added into

TABLE 1

Cell culture methods used to generate in vitro produced cell-based meat

| Method # | Sample ID | Culture Condition Cell Type(s) (ratio) | Culture format | Base media |
|---|---|---|---|---|
| 1 | *A. Platyrhynchos* (duck) fibroblast tissue 1 | Co-culture F/M (50/50) Monoculture F | Adherent | DMEM-F12 with FBS (High), DS (High), CS (Low), HS (Low) |
| 2 | *A. Platyrhynchos* (duck) fibroblast tissue 1 | Monoculture F | Adherent | DMEM-F12 with FBS (High), DS (High), CS (Low), HS (Low) |
| 3 | Bos (cow) fibroblast tissue 1 | Monoculture F | Adherent | DMEM-F12 with FBS (High), BS (High), CS (Low), HS (Low) |
| 4 | *Gallus* (chicken) fibroblast tissue 1 | Monoculture F | Adherent | DMEM-F12 with FBS (High) CS (Low) |
| 5 | *Gallus* (chicken) fibroblast tissue 2 | Monoculture F | Adherent | DMEM-F12 with CS (High), BS (Low) |
| 6 | *Gallus* (chicken) fibroblast tissue 3 | Monoculture F | Adherent | DMEM-F12 with CS (High), BS (High) |
| 7 | *Gallus* (chicken) fibroblast tissue 4 | Monoculture F | Adherent | DMEM-F12 with BS (High), CS (Low) |
| 8 | *Gallus* (chicken) fibroblast cells 1 | Monoculture F | Adherent | DMEM-F12 with 10% FBS |

In some embodiments, the media is substantially free of serum or other components derived from an animal.

Accordingly, an exemplary method of producing in vitro produced cell-based meat comprises: (a) providing fibroblasts and/or myoblasts from a non-human organism; (b)

culture thus resulting in lower or non-existent hormonal levels in a resulting cell-based meat product. Accordingly, in some embodiments, the cell-based product is substantially free of steroid hormones (i.e., contains little or no steroid hormones). This is in contrast to the animals raised for conventional meat production, which are often fed or otherwise administered exogenous hormones.

Accordingly, in some embodiments, the cell-based product of the disclosure comprises no more than about 1 ug, 0.5 ug, 0.1 ug, 0.05 ug, 0.01 ug, 0.005 ug, or even about 0.001 ug steroid hormone/kg dry mass of cell-based product. In some embodiments, the cell-based product comprises no more than about 1 ug, 0.5 ug, 0.1 ug, 0.05 ug, 0.01 ug, 0.005 ug, or even about 0.001 ug progesterone/kg dry mass of cell-based product. In some embodiments, the cell-based product comprises no more than about 1 ug, 0.5 ug, 0.1 ug, 0.05 ug, 0.01 ug, 0.005 ug, or even about 0.001 ug testosterone/kg dry mass of cell-based product. In some embodiments, the cell-based product comprises no more than about 0.05 ug, 0.01 ug, 0.005 ug, or even about 0.001 ug estradiol/kg dry mass of cell-based product. In exemplary embodiments, the cell-based product comprises no more than about 35 ng estradiol/kg dry mass of cell-based product.

Microbial Contamination

Using the sterile, laboratory-based in vitro culturing methods described, the cell-based product is substantially free of microbial contaminants. "Substantially free" means that the concentration of microbes or parasites is below a clinically significant level of contamination, i.e., below a level wherein ingestion would lead to disease or adverse health conditions. Such low levels of contamination allow for an increased shelf life. This is in contrast to animals raised for conventional meat production. As used herein, microbial contamination includes, but is not limited to, bacteria, fungi, viruses, prions, protozoa, and combinations thereof. Harmful microbes may include coliforms (fecal bacteria), *E. coli*, yeast, mold, *Campylobacter, Salmonella, Listeria*, and Staph.

In addition, cells grown in culture may be substantially free from parasites such as tapeworms that infect cells of whole animals and that are transferred to humans through consumption of insufficiently cooked meat.

Antibiotics

Relative to conventional products, in vitro produced cell-based products of the disclosure comprise a significantly lower amount of antibiotics, or are substantially free of antibiotics, or are free of antibiotics entirely. For example, using the in vitro culturing methods described, the use of antibiotics in culture can be controlled or eliminated, thus resulting in lower or non-existent antibiotic levels in the resulting cell-based product. Accordingly, in some embodiments, the cell-based product is substantially free of antibiotics (i.e., contains little or no antibiotics). This is in contrast to animals raised for conventional meat production, which are often fed or otherwise administered exogenous antibiotics.

Accordingly, in some embodiments, the cell-based product of the disclosure comprises no more than about 100 ug antibiotics/kg dry mass of cell-based product, 90 ug antibiotics/kg dry mass of cell-based product, 80 ug antibiotics/kg dry mass of cell-based product, 70 ug antibiotics/kg dry mass of cell-based product, 60 ug antibiotics/kg dry mass of cell-based product, 50 ug antibiotics/kg dry mass of cell-based product, 40 ug antibiotics/kg dry mass of cell-based product, 30 ug antibiotics/kg dry mass of cell-based product, 20 ug antibiotics/kg dry mass of cell-based product, 10 ug antibiotics/kg dry mass of cell-based product, 5 ug antibiotics/kg dry mass of cell-based product, 1 ug antibiotics/kg dry mass of cell-based product, 0.5 ug antibiotics/kg dry mass of cell-based product, 0.1 ug antibiotics/kg dry mass of cell-based product, 0.05 ug antibiotics/kg dry mass of cell-based product, or even about 0.01 ug/kg of antibiotics/kg dry mass of cell-based product.

Lipids

As compared to conventional products, the in vitro produced cell-based products of the disclosure comprise a lower average total lipid (fat) content. For example, cell-based meat generally has an average total fat content between about 0.5% to about 5.0%, whereas the fatty acid content in conventional meat varies widely and can range from about 3% to about 18%, depending on the cut of meat.

Accordingly, in some embodiments, the cell-based product of the disclosure comprises an average total fat content of about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, or about 5.0%, when measured as a % of total wet mass of the cell-based product. A lower fat content provides a lower caloric content, as well as other related health benefits, when compared to conventional products.

The methods provided herein can alter specific fatty acid profiles to achieve desired flavor characteristics or fatty acid profiles. The lower levels of fatty acids in the cell-based product of the disclosure also promotes an increased shelf life, for example by leading to lower levels of fatty oxidation in the product.

Amino Acids

The cell-based meat product of the disclosure generally comprises about 50 g to about 95 g by weight of amino acids per 100 g dry mass.

Vitamin E Content

As compared to conventional products, the in vitro produced cell-based products of the disclosure comprise a higher Vitamin E (aTocopherol) content. In some embodiments, the cell-based product of the disclosure comprises at least about 0.5 mg, at least about 0.6 mg, at least about 0.7 mg, at least about 0.8 mg, at least about 0.9 mg, or at least about 1.0 mg/Vitam in E/100 g wet mass of cell-based product.

Moisture Content

The cell-based product of the disclosure generally has a moisture content of about 65% to about 95%.

Architecture of Cell-Based Meat

By way of example, cell-based meat, unless otherwise manipulated to include, does not include vascular tissues, such as veins and arteries, whereas conventional meat does contain such vasculature, and contains the blood found in the vasculature. Accordingly, in some embodiments, the cell-based meat does not comprise any vasculature.

Likewise, cell-based meat, although composed of muscle or muscle-like tissues, unless otherwise manipulated to include, does not comprise functioning muscle tissue. Accordingly, in some embodiments, the cell-based meat does not comprise functioning muscle tissue.

It is noted that features such as vasculature and functional muscle tissue can be further engineered into the cell-based meat, should there be a desire to do so.

Supplementation

In other embodiments, other nutrients, such as vitamins, may be added to increase the nutritional value of the cell-based product. For example, this may be achieved through the exogenous addition of the nutrients to the growth medium or through genetic engineering techniques.

Shelf Life

A significant portion of meat and meat products are spoiled every year. It is estimated that approximately 3.5 billion kg of poultry and meat are wasted at the consumer, retailer and foodservice levels which have a substantial economic and environmental impact (Kantor et al. (1997)). A significant portion of this loss is due to microbial spoilage.

Conventional meat is perishable and has a relatively short shelf life stability (interchangeably referred to as simply "shelf life" herein). The shelf life is the amount of time a food remains fit for human consumption. The composition of conventional meat and the conditions used to slaughter and harvest the meat create favorable growth conditions for various microorganisms including fecal bacteria (e.g., coliform bacteria). Meat is also very susceptible to spoilage due to chemical, oxidative and enzymatic activities. It is generally regarded that microbial growth, oxidation and enzymatic autolysis are three mechanisms responsible for the spoilage of meat. The breakdown of fat, protein and carbohydrates of meat results in the development of off-odors and off-flavor and these the off-odors and off-flavors make the meat objectionable for human consumption. Depending on the species and method of harvest, conventional meat products are not safe to consume after a relatively short period of storage time. For example, chicken should be cooked within a few days of purchasing. Cooked poultry can be safely stored in the fridge for only 4 days and the freezer for up to 4 months. It is, therefore, necessary to control meat spoilage in order to increase its shelf life and maintain its nutritional value, texture and flavor.

In vitro produced cell-based meat, through its method of production and composition, produces a meat product that has extended shelf life compared to conventional meat products and does not require the addition of preservative agents to obtain the shelf life stability. The composition of cell-based meat is such that fewer off-odors and off-flavors are detected. In addition, the manufacturing methods used to produce in vitro cell-based meat require clean and aseptic conditions. These conditions ensure that microbial cell counts in both harvested products and subsequent food processing are low. These multiple factors contribute to extended shelf life stability of in vitro cell-based meat.

The shelf life due to spoilage of the cell-based meat of the disclosure is enhanced relative to conventional meat. This is the case both at room temperature (about 25° C.) and at colder temperatures (e.g., about 4° C.). The increased shelf life is associated with reduced contamination, composition of the cell-based meat, reduced degradation of the cell-based meat and slower rates of change in color, spoilage, smell and flavor of the cell-based meat Formation of the Scaffold As described above, approximately 90% by weight or greater of the scaffold comprises plant-based fats and waxes. Exemplary fats and waxes include palm kernel oil, coconut oil, cocoa butter, and palm oil. Of course, other (saturated and/or unsaturated) fats (fatty acids)/waxes may also and/or additionally be used. Known techniques to emulsify a blend of oils and fats from vegetables, for instance fractionation, interesterification and/or hydrogenation to achieve the desired properties can be applied. In some embodiments, the plant-based fats and waxes comprise approximately 98% by weight or greater of the scaffold.

In addition to the plant-based fats and waxes, the remaining approximately 10% or fewer of the scaffold comprises additional functional ingredients to help the seeded cells bind to the scaffold and to maintain the structural integrity of the scaffolds. These functional ingredients should have similar functions as their naturally occurring counterparts that are found on the cell surfaces/in the cell membranes. Exemplary ingredients include binding/signaling proteins such as selectine, cadherine, integrine, claudine, and connexin; carbohydrates such as sugars, starches, and pectin; fibers such as cellulose fibers, fungal mycelia, and algae; vitamins and minerals to help promote cellular growth; and gases such as air, nitrogen and oxygen. In some embodiments, the additional functional ingredients comprise approximately 2% by weight or lower of the scaffold. In some instances, the functional ingredients in the scaffold are limited such that the combination of exposure to the growth media and exposure to a melted scaffold do not result in excessive or unacceptable osmotic stress on the growing cells.

To prevent contamination of the cell-based meats during the growth phase, the scaffolds should be easily sterilized via the heating of the scaffold prior to the cellular growth phase. The plant-based-fats (mostly saturated fatty acids) and/or waxes are therefore heated to a sterilization temperature above their melting and below their smoking point. Other substances may be individually sterilized and/or added to the suspension. The required time and sterilization temperature for the thermal sterilization process should be chosen according to the potential harmful microbes and spores (D- and Z-value), and may also be adjusted to the stabilization of other ingredients (like denaturalization temperature of enzymes and vitamins). The D-value of an organism is the time required in a given medium, at a given temperature, for a ten-fold reduction in the number of organisms, while the Z-value is the number of degrees the temperature has to be increased to achieve a tenfold (i.e. 1 $\log_{10}$ reduction in the D-value. If a sterile filtration of the product is additionally or alternatively foreseen to the heat sterilization, all used substances should be soluble/meltable.

After the sterilization of all ingredients are complete, the scaffold can be cooled down to an incorporation temperature before scaffold formation. Other sterile ingredients including gases, may be injected into the mixture, either before or after cooling, to maintain their chemical-physical properties (such as the functionalities of proteins and/or crystalline structure). The creation of the scaffold itself is caused by dispersion and cooling. In some embodiments, cold gases are used to solidify the mixture. In some embodiments, sterile powders and minerals could be used as seeds, and/or coats for example in spray dry reactors. Multiple scaffold layers with different properties can be created in those units, also by alternating different suspensions and variations of ingredients.

Although using gas dispersion and cooling to form the scaffold enables the creation of functional and specifically designed scaffolds, the process is complex and costly. Therefore, in other embodiments, the scaffolds can be solidified by dispersing them into a cold, sterile fluid, such as water or media (with or without the cells contained in it), to be better suitable for the mass production of cell-based meat.

In some embodiments, the melted, liquid scaffold can be injected into the colder fluid to form thin strands of scaffolding material. In other embodiments, the scaffold is sprayed onto the colder fluid, creating a high number of small droplets with a large surface for cell adherence. As these sterile, functional scaffolds are very valuable, they may be produced and utilized at different times, or in different facilities if desired.

In certain embodiments, the plant-fat-based, functional scaffold, which is formed by cooling the previously heat-sterilized ingredients down to solidify them at least partially, is processed at temperatures, in which cells can bind to the contained proteins, fuse, and form tissue. The seeding can thereby be done in an environment that is colder than the optimal growth temperature of the cells, to assure the structure of the scaffold. Alternatively, the seeding can be done at or above the optimal growth temperature of the cells when the scaffold is at least partially melted. To ensure that the seeded cells are capable of adhering to the scaffold, cell-binding proteins are also added to the scaffold during the seeding phase. After the scaffold has been seeded with a desired population of cells, the seeded scaffold is then immersed into a nutrient-rich broth to incentivize cellular growth.

Because the scaffold has a melting point lower than the upper end of the temperature endurance range of the seeded cells, the temperature can be raised during the cellular growth phase to the point in which the scaffold partially melts without damaging the cells, which provides the seeded cells with greater exposure to the nutrient-rich environment in which the seeded scaffold is immersed. This allows more space for the cultivated cells to grow and also exposes the cultivated cells to more nutrients to assist with cellular growth. In some embodiments, the scaffold itself contains additional vitamins and minerals that incentivize cellular growth. These additional vitamins and minerals may be released as the scaffold melts. In one example, the scaffold melting releases nutrients stored in the scaffold, allows cells greater access to the media flow and the nutrients therein, provides increased space for the cells to grow into, or some combination thereof. In other embodiments, a constant temperature within the optimal growth temperature range of the seeded cells is chosen that is below the melting point of the scaffold so that the scaffold does not melt during the cellular growth phase.

After the desired biomass and degree of tissue formation/cellular fusion is achieved, in some embodiments, the scaffold is left entirely into the final product as it is safe for consumption. In other embodiments, the scaffold can be partially or completely melted out of the final product prior to the harvesting of the cell tissue.

If the scaffold is melted out, the melted scaffold material may be recycled using any known conventional means, such as via a wastewater treatment plant. Alternatively, because the melted scaffold material can be separated easily due to its low density, in some embodiments, the melted scaffold material can be separated and reused as new scaffolding material.

In some embodiments, the scaffold is created in a self-enclosed bioreactor comprising of a sterilization system for the tanks in fluid communication with the reaction chamber, and one or more spray nozzles capable of delivering one or more of the sterilized plant-based fats, cell-binding proteins, culture media, and cultivated cells.

EXAMPLES

Example 1: Emulsified Coconut Oil Scaffold for the Growth of Mammalian Meat

In one non-limiting example, a mixture comprising 90% or greater of emulsified coconut, and 10% or less of selectine, cellulose fiber, and pectin is heated to a temperature above 65 degrees Celsius for up to 30 minutes to sterilize the mixture. Higher temperatures of sterilization can be used in order to reduce the time period of sterilization. The mixture is then cooled to the incorporation temperature by spraying the mixture into a bioreactor containing a 15 degree Celsius nutrient media in order to form a high number of droplet scaffolds. Additional functional ingredients, including cell-binding proteins, sugars, vitamins, and minerals are added to the bioreactor via transfer line or nozzle. In vitro prepared mammalian meat cells are then seeded onto the scaffold until a desired population is reached. The temperature is then raised to between 30 and 40 degrees Celsius, the optimal cellular growth temperature for mammalian cells, and the seeded cells are allowed to grow. In some instances, the temperature is raised temporarily to 41-43 degrees Celsius until a desired portion of the scaffolding material melts out of the cellular tissue, releasing additional sugars, vitamins, and minerals from the scaffold into the media to assist in cell growth, before being lowered back down to the optimal growth temperature. The cellular tissue is then extracted out of the bioreactor while the melted scaffolding is melted out of the final product and separated from the aqueous solution using known density filtration methods. Alternatively, the scaffold is removed from the cellular tissue without being melted. In a further alternative, the scaffold is edible and remains as a part of the cellular tissue.

What is claimed is:

1. A cell-based food product for human consumption, said cell-based food product comprising:
    a plurality of dispersed plant fat-based droplet scaffolds comprising (a) at least one plant-based saturated fatty acid or wax from droplets of a liquid that transitions from a sterilization temperature to an incorporation temperature; and (b) a cell binding protein that enables adherence of tissue cells to the plurality of dispersed plant fat-based droplet scaffolds for growth;
    wherein the plurality of dispersed plant fat-based droplet scaffolds exists in a liquid state at the sterilization temperature of the at least one plant-based saturated fatty acid or wax; and wherein the plurality of dispersed plant fat-based droplet scaffolds exists in a solid state at the incorporation temperature and during cell adhesion and growth; and
    grown non-human muscle, skin, or fat derived cells.

2. The cell-based food product of claim 1, wherein the plurality of dispersed plant fat-based droplet scaffolds is edible.

3. The cell-based food product of claim 1, further comprising one or more secondary components chosen from nutrients and minerals to promote cellular growth, preservatives, coloring agents, flavor increasers, cell binding assistance molecules, and structural support components.

4. The cell-based food product of claim 1, wherein the grown non-human muscle, skin, or fat derived cells comprise at least one of myoblasts, myocytes, skeletal muscle progenitor cells, side population cells, mesoangioblasts, mesenchymal stem cells, fibroblasts, pericytes, adipocytes, or pluripotent stem cells.

5. A method for forming a plurality of dispersed plant fat-based droplet scaffolds designed for growth of cell-based non-human tissue for human consumption, said method comprising:
    a. providing droplets of a liquid comprising at least one plant-based saturated fatty acid or wax to form a plurality of plant fat-based liquid droplets;
    b. sterilizing the plurality of plant fat-based liquid droplets at least partially by heating the at least one plant-based saturated fatty acid or wax to above a melting point at which the at least one plant-based saturated fatty acid or wax is in liquid state and below a smoking point of the at least one plant-based saturated fatty acid or wax;

c. dispersing the plurality of plant fat-based liquid droplets in a lower temperature fluid or gas to form a plurality of dispersed solid droplet scaffolds;

d. seeding the plurality of dispersed solid droplet scaffolds with a population of non-human muscle, skin, or fat derived cells for growth; and e. melting the plurality of dispersed solid droplet scaffolds at a melting temperature within an endurance range of seeded cells to separate at least a portion of the plurality of dispersed solid droplet scaffolds from cells of the population of non-human muscle, skin, or fat derived cells attached to the plurality of dispersed solid droplet scaffolds.

6. The method of claim 5, wherein the plurality of dispersed plant fat-based droplet scaffolds is removable, either partially or completely, from the non-human muscle, skin, or fat derived cells by melting the plurality of dispersed plant fat-based droplet scaffolds back into a liquid phase and separating the plurality of dispersed plant fat-based droplet scaffolds in the liquid phase from the cells of the population of non-human muscle, skin, or fat derived cells.

7. The method of claim 6, wherein, after separating at least the portion of the plurality of dispersed plant fat-based droplet scaffolds from the non-human muscle, skin, or fat derived cells, at least the portion of the plurality of dispersed plant fat-based droplet scaffolds is recycled or reused as raw material for a formation of another plurality of dispersed plant fat-based droplet scaffolds.

8. The method of claim 6, wherein the population of non-human muscle, skin, or fat derived cells comprise at least one of myoblasts, myocytes, skeletal muscle progenitor cells, side population cells, mesoangioblasts, mesenchymal stem cells, fibroblasts, pericytes, adipocytes, or pluripotent stem cells.

9. A method for growing cell-based food products from a population of non-human muscle, skin, or fat derived cells using a plurality of dispersed plant fat-based droplet scaffolds, said method comprising:

a. providing a plurality of dispersed plant fat-based droplet scaffolds comprising at least one saturated fatty acid or wax and a cell binding protein;

b. seeding the plurality of dispersed plant fat-based droplet scaffolds with a population of non-human muscle, skin, or fat derived cells;

c. supplying the population of non-human muscle, skin, or fat derived cells with one or more growth nutrients;

d. growing the population of non-human muscle, skin, or fat derived cells to reach a desired size or shape; and e. melting the plurality of dispersed plant fat-based droplet scaffolds at a melting temperature within an endurance range of seeded cells to separate the plurality of dispersed plant fat-based droplet scaffolds from cells of the population of non-human muscle, skin, or fat derived cells attached to the plurality of dispersed plant fat-based droplet scaffolds.

10. The method of claim 9, wherein the non-human muscle, skin, or fat derived cells may be supplied with one or more growth nutrients to expedite growth.

11. The method of claim 10, wherein the one or more growth nutrients is incorporated into the plurality of dispersed plant fat-based droplet scaffolds.

12. The method of claim 11, wherein the plurality of dispersed plant fat-based droplet scaffolds comprising the one or more growth nutrients has a melting temperature below an upper limit of a growth temperature range of the seeded cells and below an upper end of the endurance range of the seeded cells, and by raising a temperature to the melting temperature during a growth phase, the plurality of dispersed plant fat-based droplet scaffolds at least partially melts and releases the one or more growth nutrients.

13. The method of claim 9, wherein the population of non-human muscle, skin, or fat derived cells comprise at least one of myoblasts, myocytes, skeletal muscle progenitor cells, side population cells, mesoangioblasts, mesenchymal stem cells, fibroblasts, pericytes, adipocytes, or pluripotent stem cells.

14. The method of claim 9, wherein the endurance range of the seeded cells comprises between 10 degrees Celsius and 55 degrees Celsius.

15. A method for growing cell-based non-human tissue product with a plurality of dispersed plant fat-based droplet scaffolds, said method comprising:

a. introducing a plurality of dispersed plant fat-based droplet scaffolds comprising at least one plant-based fats or waxes;

b. seeding the plurality of dispersed plant fat-based droplet scaffolds with a population of cells, comprising of non-human muscle, skin, or fat derived cells having an initial mass, while the plurality of dispersed plant fat-based droplet scaffolds is partially solid and partially liquid;

c. cooling the plurality of dispersed plant fat-based droplet scaffolds into a plurality of dispersed plant fat-based solid droplet scaffolds after the population of cells are seeded;

d. growing the population of cells for at least a time period, wherein the population of cells reach a mass greater than the initial mass; and e. harvesting a cell-based food product comprising the plurality of dispersed plant fat-based solid droplet scaffolds and cells from the population of cells.

16. The method of claim 15, wherein the plurality of dispersed plant fat-based droplet scaffolds comprises two or more different types of fats or waxes, each having different melting temperatures.

17. The method of claim 16, wherein seeding the plurality of dispersed plant fat-based droplet scaffolds comprises seeding the plurality of dispersed plant fat-based droplet scaffolds while at least one plant-based fat or wax is in a liquid state and at least one plant-based fat or wax is in a solid state.

18. The method of claim 15, wherein the plurality of dispersed plant fat-based droplet scaffolds forms a solid at a growing temperature of the populations of cells.

19. The method of claim 15, further comprising introducing one or more cell binding proteins while the plurality of dispersed plant fat-based droplet scaffolds is partially solid and partially liquid.

20. The method of claim 15, wherein the non-human muscle, skin, or fat derived cells comprise at least one of myoblasts, myocytes, skeletal muscle progenitor cells, side population cells, mesoangioblasts, mesenchymal stem cells, fibroblasts, pericytes, adipocytes, or pluripotent stem cells.

* * * * *